(12) United States Patent
Anderson et al.

(10) Patent No.: US 8,192,402 B2
(45) Date of Patent: Jun. 5, 2012

(54) ACCESS DEVICE

(75) Inventors: Janelle Anderson, New York, NY (US); Michael Tal, Woodbridge, CT (US); Steven F. Bierman, Del Mar, CA (US)

(73) Assignee: Access Scientific, Inc., San Diego, CA (US)

( * ) Notice: Subject to any disclaimer, the term of this patent is extended or adjusted under 35 U.S.C. 154(b) by 1076 days.

(21) Appl. No.: 12/106,119

(22) Filed: Apr. 18, 2008

(65) Prior Publication Data

US 2008/0262430 A1  Oct. 23, 2008

Related U.S. Application Data

(60) Provisional application No. 60/912,645, filed on Apr. 18, 2007, provisional application No. 60/948,136, filed on Jul. 5, 2007.

(51) Int. Cl.
*A61M 5/178* (2006.01)
*A61M 25/16* (2006.01)
*A61M 25/18* (2006.01)
*A61M 39/00* (2006.01)
*A61M 39/10* (2006.01)
*A61M 39/02* (2006.01)

(52) U.S. Cl. ........... 604/164.1; 604/164.13; 604/165.03; 604/166.01; 604/535; 604/538

(58) Field of Classification Search ........... 604/165.01–165.04, 164.01, 164.04, 604/164.07, 523, 533, 534, 535, 538, 539
See application file for complete search history.

(56) References Cited

U.S. PATENT DOCUMENTS 3,539,034 A * 11/1970 Tafeen .................. 604/164.09
3,565,074 A    2/1971 Foti et al.
3,995,628 A   12/1976 Gula et al.

(Continued)

FOREIGN PATENT DOCUMENTS

EP        0139091        7/1984

(Continued)

OTHER PUBLICATIONS

Arrow Trauma Products No. TRM-C 12/00 11M, Arrow International.
International Search Report for PCT Application No. PCT/US/2006/011624, mailed Oct. 17, 2007.
International Search Report for PCT Application No. PCT/US/2002/041371, mailed Oct. 2, 2003.
A photograph of various access devices.
Office Action from EP 08746350.1-2310, dated Jun. 17, 2011.

(Continued)

*Primary Examiner* — Kevin C Sirmons
*Assistant Examiner* — William Carpenter
(74) *Attorney, Agent, or Firm* — Knobbe, Martens, Olson & Bear LLP

(57) ABSTRACT

An access device places a medical article within a body space of a patient. The device has a needle that includes a needle body and hub. The device further includes a dilator coaxially disposed and slideable over the needle body and a medical article. A viewing space is disposed between the dilator and the medical article with at least one passageway or conduit connecting the viewing space with the interior bore of the needle body. The passageway is defined at least in part by openings through the sides of the needle and dilator. At least a portion of the conduit or passageway can be defined by one or more grooves between the needle and dilator. The device can further include a guidewire and an interlock between the guidewire and the needle and/or dilator. The device can further include one or more stops disposed between the guidewire and the needle and/or dilator to limit the extent to which the guidewire can be moved (e.g., advanced) relative to the needle or inhibit such relative movement (e.g., backwards movement).

58 Claims, 10 Drawing Sheets

U.S. PATENT DOCUMENTS

| | | | | |
|---|---|---|---|---|
| 4,068,659 | A | 1/1978 | Moorehead | |
| 4,205,675 | A | 6/1980 | Vaillancourt | |
| 4,230,123 | A * | 10/1980 | Hawkins, Jr. | 600/435 |
| 4,345,596 | A * | 8/1982 | Young | 604/264 |
| 4,411,655 | A | 10/1983 | Schreck | |
| 4,417,886 | A | 11/1983 | Frankhouser et al. | |
| 4,512,351 | A * | 4/1985 | Pohndorf | 607/117 |
| 4,525,157 | A | 6/1985 | Vaillancourt | |
| 4,581,019 | A * | 4/1986 | Curelaru et al. | 604/164.05 |
| 4,629,450 | A | 12/1986 | Suzuki et al. | |
| 4,655,750 | A | 4/1987 | Vaillancourt | |
| 4,661,300 | A | 4/1987 | Daugherty | |
| 4,772,264 | A * | 9/1988 | Cragg | 604/158 |
| 4,791,937 | A | 12/1988 | Wang | |
| 4,850,975 | A | 7/1989 | Furukawa | |
| 4,869,259 | A | 9/1989 | Elkins | |
| 4,894,052 | A | 1/1990 | Crawford | |
| 4,944,728 | A | 7/1990 | Carrell | |
| 4,955,890 | A | 9/1990 | Yamamoto et al. | |
| 4,961,729 | A | 10/1990 | Vaillancourt | |
| 4,978,334 | A | 12/1990 | Toye et al. | |
| 4,995,866 | A | 2/1991 | Amplatz et al. | |
| 5,066,284 | A | 11/1991 | Mersch et al. | |
| 5,098,392 | A * | 3/1992 | Fleischhacker et al. | 604/164.05 |
| 5,108,374 | A | 4/1992 | Lemieux | |
| 5,112,308 | A | 5/1992 | Olsen et al. | |
| 5,114,401 | A | 5/1992 | Stuart et al. | |
| 5,158,544 | A | 10/1992 | Weinstein | |
| 5,171,218 | A | 12/1992 | Fonger et al. | |
| 5,242,410 | A | 9/1993 | Melker | |
| 5,242,427 | A | 9/1993 | Bilweis | |
| 5,246,426 | A | 9/1993 | Lewis et al. | |
| 5,250,038 | A | 10/1993 | Melker et al. | |
| 5,255,691 | A * | 10/1993 | Otten | 607/117 |
| 5,295,969 | A | 3/1994 | Fischell | |
| 5,295,970 | A | 3/1994 | Clinton et al. | |
| 5,306,253 | A | 4/1994 | Brimhall | |
| 5,312,355 | A | 5/1994 | Lee | |
| 5,328,480 | A | 7/1994 | Melker et al. | |
| 5,330,433 | A | 7/1994 | Fonger et al. | |
| 5,336,191 | A * | 8/1994 | Davis et al. | 604/165.01 |
| 5,342,315 | A | 8/1994 | Rowe et al. | |
| 5,366,441 | A | 11/1994 | Crawford | |
| 5,380,290 | A | 1/1995 | Makower et al. | |
| 5,391,178 | A | 2/1995 | Yapor | |
| 5,512,052 | A * | 4/1996 | Jesch | 604/158 |
| 5,542,932 | A | 8/1996 | Daugherty | |
| 5,589,120 | A | 12/1996 | Khan et al. | |
| 5,676,689 | A | 10/1997 | Kensery et al. | |
| 5,685,856 | A * | 11/1997 | Lehrer | 604/164.1 |
| 5,688,249 | A | 11/1997 | Chang et al. | |
| 5,704,914 | A | 1/1998 | Stocking et al. | |
| 5,712,229 | A | 1/1998 | Hopkins et al. | |
| 5,728,132 | A | 3/1998 | Van Tassel et al. | |
| 5,795,339 | A | 8/1998 | Erskine | |
| 5,810,780 | A | 9/1998 | Brimhall et al. | |
| 5,820,596 | A | 10/1998 | Rosen et al. | |
| 5,827,202 | A | 10/1998 | Miraki et al. | |
| 5,830,190 | A | 11/1998 | Howell | |
| 5,833,662 | A | 11/1998 | Stevens | |
| 5,858,002 | A | 1/1999 | Jesch | |
| 5,885,217 | A | 3/1999 | Gisselberg et al. | |
| 5,885,253 | A | 3/1999 | Liu | |
| 5,904,657 | A | 5/1999 | Unsworth et al. | |
| 5,910,132 | A | 6/1999 | Schultz | |
| 5,919,160 | A | 7/1999 | Sanfilippo | |
| 5,935,110 | A | 8/1999 | Brimhall | |
| 5,954,708 | A * | 9/1999 | Lopez et al. | 604/533 |
| 6,027,480 | A | 2/2000 | Davis et al. | |
| 6,046,143 | A | 4/2000 | Khan et al. | |
| 6,074,377 | A | 6/2000 | Sanfilippo | |
| 6,080,141 | A | 6/2000 | Castro et al. | |
| 6,120,494 | A | 9/2000 | Jonkman | |
| 6,156,010 | A | 12/2000 | Kuracina et al. | |
| 6,159,179 | A | 12/2000 | Simonson | |
| 6,179,813 | B1 | 1/2001 | Ballow et al. | |
| 6,210,366 | B1 | 4/2001 | Sanfilippo | |
| 6,273,871 | B1 | 8/2001 | Davis et al. | |
| 6,277,100 | B1 | 8/2001 | Raulerson | |
| 6,336,914 | B1 * | 1/2002 | Gillespie, III | 604/165.01 |
| 6,436,070 | B1 | 8/2002 | Botich et al. | |
| 6,461,362 | B1 | 10/2002 | Halseth et al. | |
| 6,475,207 | B1 | 11/2002 | Maginot | |
| 6,488,662 | B2 | 12/2002 | Sirimanne | |
| 6,500,152 | B1 | 12/2002 | Illi | |
| 6,524,277 | B1 | 2/2003 | Chang | |
| 6,607,511 | B2 | 8/2003 | Halseth et al. | |
| 6,626,868 | B1 | 9/2003 | Prestidge et al. | |
| 6,641,564 | B1 * | 11/2003 | Kraus | 604/164.1 |
| 6,692,462 | B2 | 2/2004 | Mackenzie et al. | |
| 6,692,482 | B2 | 2/2004 | Heller et al. | |
| 6,695,816 | B2 | 2/2004 | Cassidy | |
| 6,726,659 | B1 | 4/2004 | Stocking et al. | |
| 6,808,520 | B1 | 10/2004 | Fourkas | |
| 6,836,687 | B2 | 12/2004 | Kelley | |
| 6,905,481 | B2 | 6/2005 | Sirimanne | |
| 6,994,693 | B2 | 2/2006 | Tal | |
| 7,001,396 | B2 | 2/2006 | Glazier et al. | |
| 7,025,746 | B2 | 4/2006 | Tal | |
| 7,182,755 | B2 | 2/2007 | Tal | |
| 7,192,433 | B2 * | 3/2007 | Osypka et al. | 606/108 |
| 7,270,649 | B2 | 9/2007 | Fitzgerald | |
| 7,503,596 | B2 * | 3/2009 | Rome et al. | 285/384 |
| 7,556,617 | B2 | 7/2009 | Voorhees, Jr. et al. | |
| 7,722,567 | B2 * | 5/2010 | Tal | 604/164.01 |
| 7,922,696 | B2 | 4/2011 | Tal et al. | |
| 2002/0072712 | A1 | 6/2002 | Nool et al. | |
| 2003/0032927 | A1 | 2/2003 | Halseth et al. | |
| 2003/0088212 | A1 | 5/2003 | Tal | |
| 2003/0171718 | A1 | 9/2003 | DeLegge | |
| 2003/0199827 | A1 | 10/2003 | Thorne | |
| 2003/0216771 | A1 | 11/2003 | Osypka et al. | |
| 2004/0092879 | A1 | 5/2004 | Kraus et al. | |
| 2004/0171988 | A1 | 9/2004 | Moretti | |
| 2004/0193112 | A1 * | 9/2004 | Glazier et al. | 604/164.1 |
| 2007/0282300 | A1 | 12/2007 | Attawia et al. | |
| 2008/0262431 | A1 | 10/2008 | Anderson et al. | |
| 2009/0221961 | A1 | 9/2009 | Tal et al. | |
| 2011/0009827 | A1 | 1/2011 | Bierman et al. | |
| 2011/0021994 | A1 | 1/2011 | Anderson et al. | |

FOREIGN PATENT DOCUMENTS

| | | |
|---|---|---|
| EP | 0502714 | 11/1995 |
| EP | 806221 | 11/1997 |
| KR | 20050027359 | 3/2005 |
| WO | WO 02/36179 A2 | 5/2002 |
| WO | WO/03057272 | 7/2003 |
| WO | WO/2007/046850 | 4/2007 |
| WO | WO 2010/048449 | 4/2010 |
| WO | WO 2010/056906 | 5/2010 |
| WO | WO 2010/083467 | 7/2010 |
| WO | WO 2010/132608 | 11/2010 |

OTHER PUBLICATIONS

Photos of a peripheral emergency infusion device Applicant believes to be produced by Arrow International Inc.

Photos of a splittable catheter design.

Photos of an infusion device Applicant believes to be produced by B. Braun Medical Inc.

Results of Preliminary Report of PCT/US2008/060914 filed Apr. 18, 2008, mailed Oct. 29, 2009.

Examination Report for European Application No. 02806219.8-2310 dated Sep. 18, 2007.

Examination Report for European Application No. 02806219.8-2310 dated May 16, 2008.

Results of Partial International Search for PCT Application No. PCT/US/2008/060930, mailed Oct. 29, 2008.

Results of Partial International Search for PCT Application No. PCT/US/2008/060914, mailed Oct. 29, 2008.

International Search Report for PCT Application No. PCT/US/2008/051950, mailed Oct. 22, 2008.

* cited by examiner

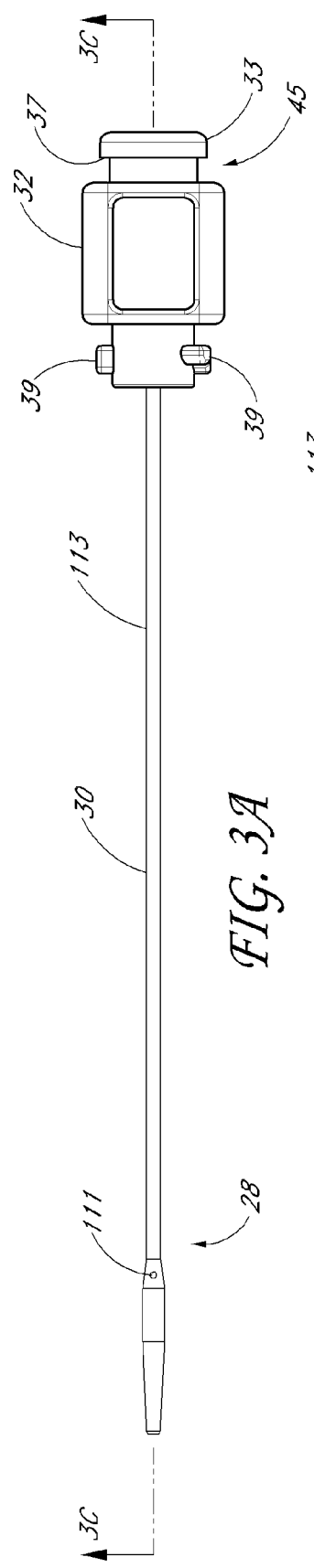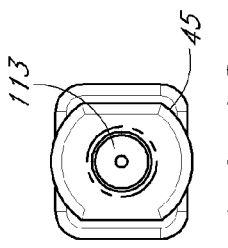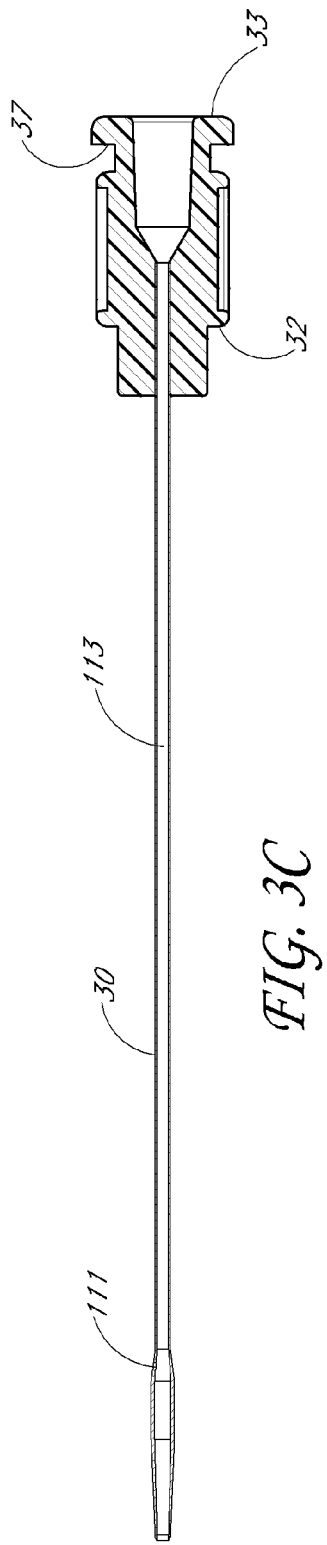
FIG. 3A
FIG. 3B
FIG. 3C

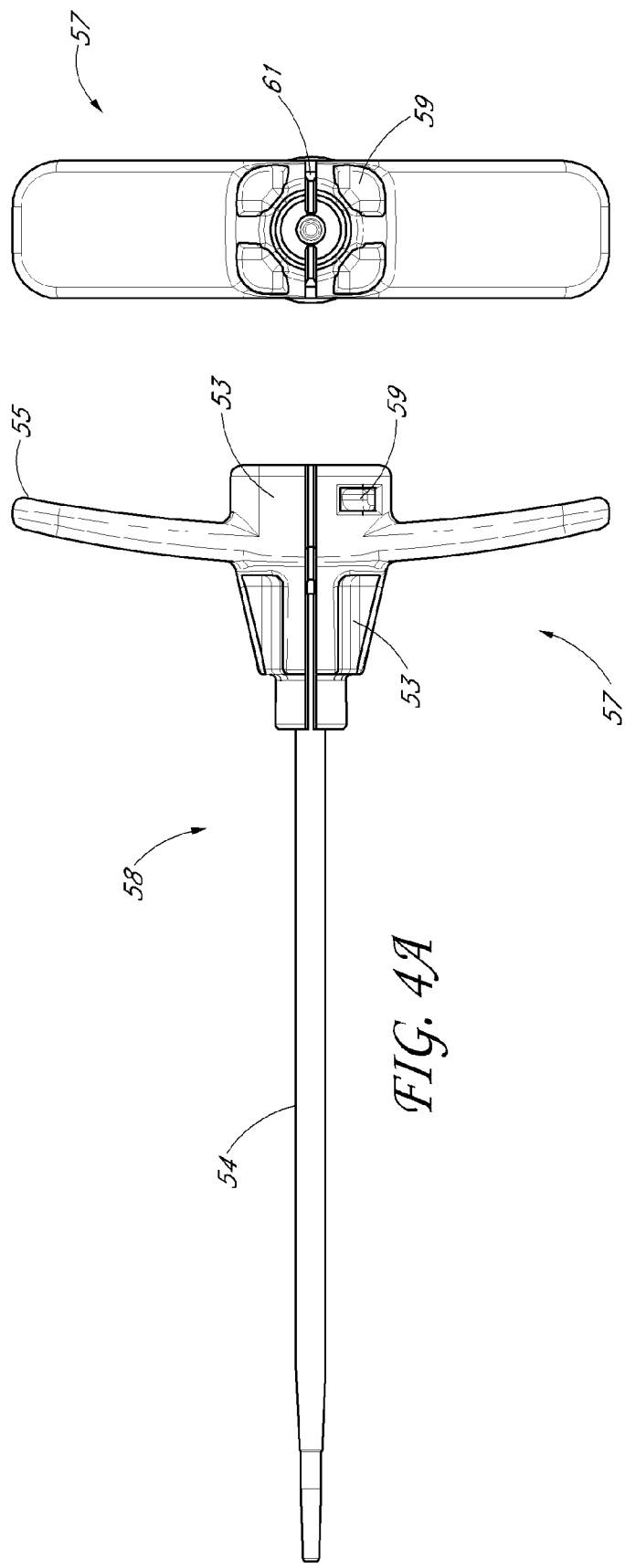
FIG. 4A
FIG. 4B
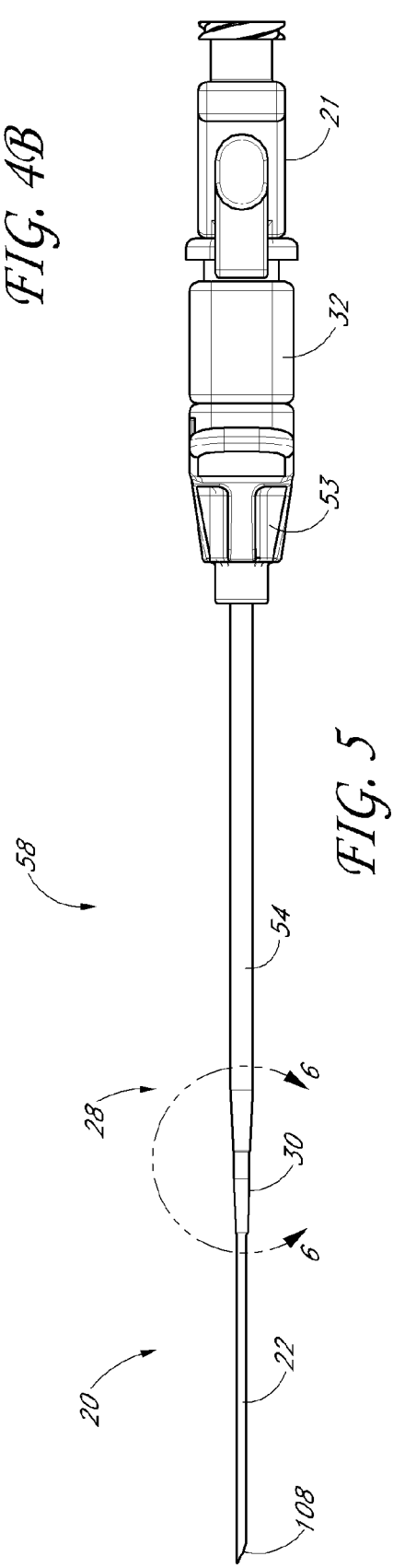
FIG. 5

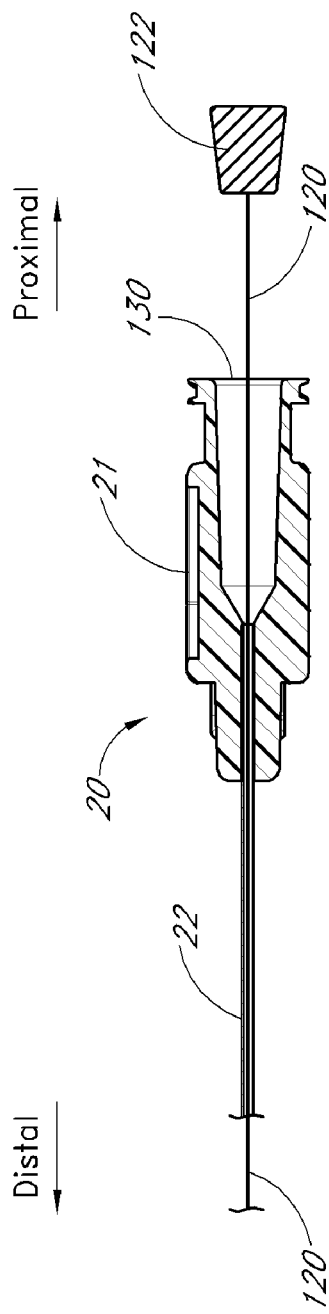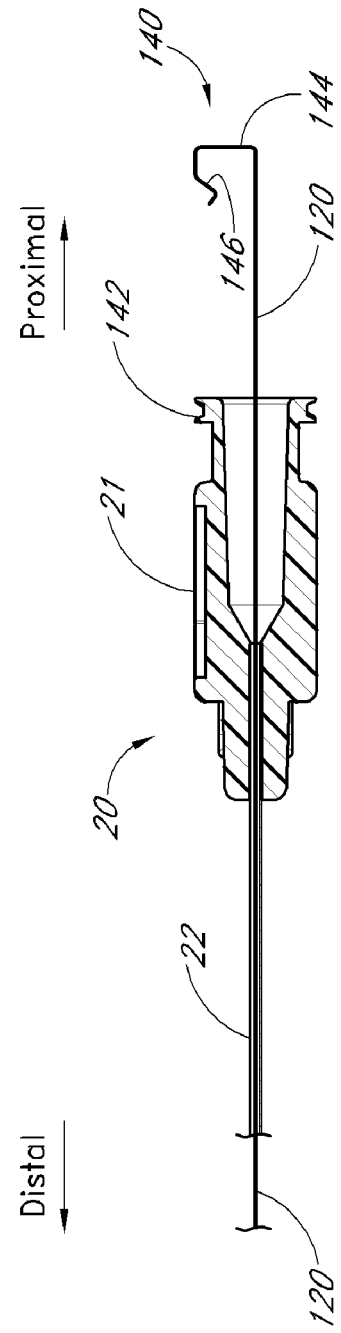

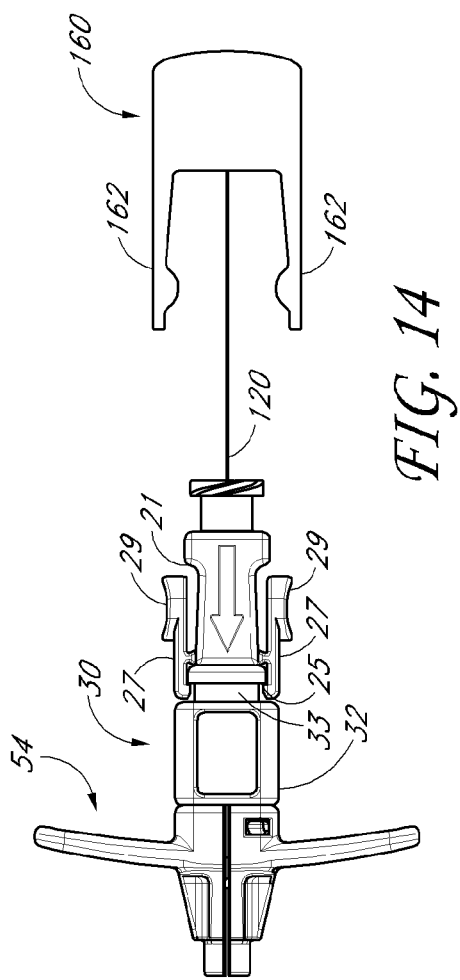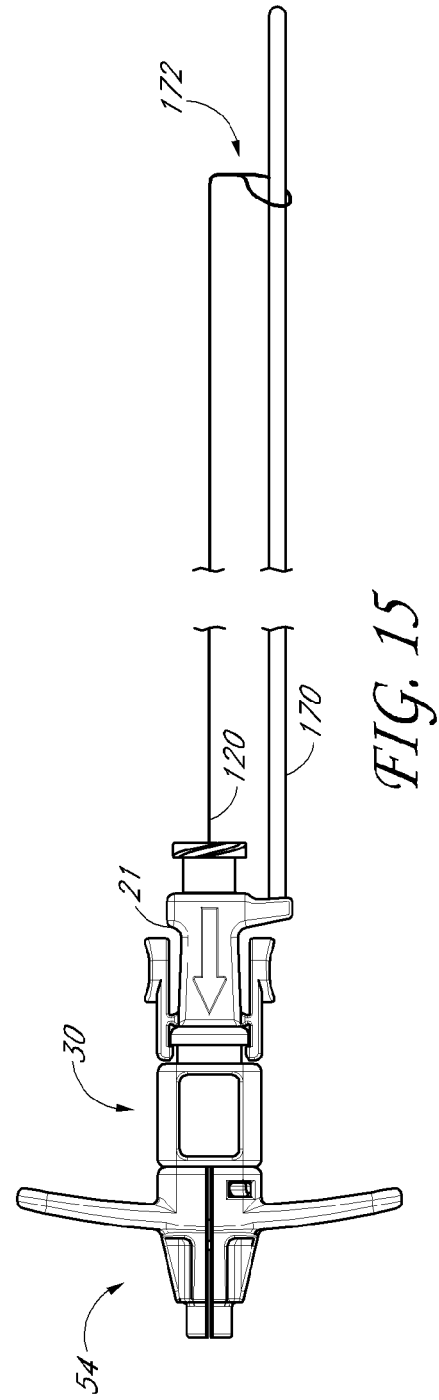

US 8,192,402 B2

ACCESS DEVICE

CROSS-REFERENCE TO RELATED APPLICATIONS

This application is related to and claims the benefit under 35 U.S.C. §119(e) to U.S. Provisional Patent Application Ser. No. 60/912,645 (filed Apr. 18, 2007) and 60/948,136 (filed Jul. 5, 2007), all of which are hereby expressly incorporated by reference in their entireties.

BACKGROUND

1. Field of the Invention

This invention is generally directed to access devices for introducing and/or delivering a medical article (such as, for example, a catheter, cannula, sheath, etc.) into a body space, such as, for example, an artery, vein, vessel, body cavity, or drainage site.

2. Description of the Related Art

A preferred non-surgical method for inserting a catheter or vascular sheath into a blood vessel involves the use of the Seldinger or a modified Seldinger technique, which includes an access needle that is inserted into a patient's blood vessel. A guidewire is inserted through the needle and into the vessel. The needle is removed, and a dilator and sheath in combination or separately are then inserted over the guidewire. The dilator and sheath, together or separately, are then inserted a short distance through the tissue into the vessel, after which the dilator and guidewire are removed and discarded. A catheter or other medical article may then be inserted through the sheath into the vessel to a desired location, or the sheath may simply be left in the vessel.

A number of vascular access devices are known. U.S. Pat. Nos. 4,241,019, 4,289,450, 4,756,230, 4,978,334, 5,124,544, 5,424,410, 5,312,355, 5,212,052, 5,558,132, 5,885,217, 6,120,460, 6,179,823, 6,210,332, 6,726,659 and 7,025,746 disclose examples of such devices. None of these devices, however, has the ease and safety of use that physicians and other healthcare providers would prefer. Thus, there exists a need for an easier-to-use and safer vascular access device, especially one that would clearly and promptly indicate when a blood vessel has been punctured and one that would reduce accidental needle sticks and other attendant risks of over-wire vascular access.

SUMMARY

Embodiments of the present invention involve several features for an access device useful for the delivery of a catheter or sheath into a space within a patient's body, such as, for example, a blood vessel or drainage site. Without limiting the scope of this invention, its more prominent features will be discussed briefly. After considering this discussion, and particularly after reading the Detailed Description of the Preferred Embodiments section below in combination with this section, one will understand how the features and aspects of this invention provide several advantages over prior access devices.

One aspect of the present invention involves an access device for placing a medical article within a body space. The device includes a needle having a needle body and a dilator coaxially disposed about the needle body and having a dilator shaft. The device further includes a medical article coaxially disposed about the dilator and a plurality of openings extending through a side of at least one of the needle body and the dilator shaft. The device further includes at least one opening in the other one of the needle body and dilator shaft. The plurality of openings are spaced about the one of the needle body or dilator shaft so that at least one of the plurality of openings at least partially overlaps the at least one opening in the other one of the needle body and dilator shaft when the needle body is rotationally clocked relative to the dilator shaft in a first position and in a second position. The second position is different than the first position. The device further includes a viewing space disposed between the dilator and the medical article and at least one passageway connecting the viewing space with an interior bore of the needle body. The passageway is defined at least in part by the plurality of openings and the at least one opening.

In some embodiments, these side openings are aligned or are overlapped to permit the flow of blood or other body fluid from the needle to the viewing space. In other embodiments, the side openings can be configured to overlap regardless of the rotational orientation of the dilator relative to the needle. For example, by irregularly spacing and/or slotting the side openings in one or both of the needle and the dilator, one or more passageways through the side walls of the needle and dilator can be provided.

In some embodiments, the conduit or passageway is (although need not be) formed between the side openings in the dilator and the needle to connect the interior bore of the needle body with the viewing space. At least a portion of the conduit or passageway can be defined by one or more grooves that are formed (e.g., by scoring) on an outer side surface of the needle, on an inner side surface of the dilator surface, or on both the needle outer side surface and the dilator inner side surface. In this latter form, the grooves can oppose each other or can overlap at one or more points to define a portion of the passageway.

In additional embodiments, the conduit or passageway that places the side openings in communication can be formed by incongruous shapes (e.g., incongruous radial cross-sectional shapes) between the needle outer surface and the dilator inner surface. For example, the needle outer surface can have a circular shape and the dilator inner surface can have an oval shape with a minor dimension of the oval substantially equals the diameter to the circle, or vise versa. The needle outer surface and the dilator inner surface also can have other incongruous shapes, such as, but without limitation, a triangle and a circle, a square and a circle, and a square and a triangle, where the needle supports the dilator at least at two points.

The viewing space, which occurs between an inner surface of the sheath and an outer surface of the dilator, can have an annular shape and can have an axial length that is almost coextensive with the length of the sheath. In other embodiments, the annular space can be significantly smaller than the elongated annular space just described. For example, but without limitation, the space can take the form of one or more annular grooves (or a fraction(s) of such an annular groove(s)) that is or are disposed at a distal, mid and/or proximal portion(s) of the sheath. For example, but without limitation, a groove can be formed on an outer surface the dilator with the side opening extending from a bottom of the groove through the side of the dilator. The space alternatively can have a linear, curved or spiral shape along an axial length of the sheath or can be formed by a plurality of such shapes. For example, one or more axial and/or spiral grooves can be formed (e.g., by scoring) on an outer side surface of the dilator, on an inner side surface of the sheath, or on both the dilator outer side surface and the sheath inner side surface. In this latter form, the grooves can oppose each other or can overlap at one or more points to define the passageway.

Another aspect of the present invention involves an access device for placing a medical article within a body space. The device includes a needle that has a needle body, a dilator coaxially disposed about the needle body and that has a dilator shaft. The device further includes a guidewire and an interlock between the guidewire and at least one of the needle and the dilator.

The interconnection or interlock may comprise an attachment connecting the guidewire to at least one area on the needle body, needle hub, and/or dilator hub. Additionally, the interconnection or interlock may comprise an attachment to the guidewire so that the guidewire cannot be totally retracted into the bevel tip or inadvertently advanced too far, resulting in intravascular guidewire loss.

The interlock or interconnection can be configured to maintain a guidewire length beyond the needle tip when advanced. The length of guidewire extension beyond the bevel tip is sufficient to prevent unwanted or accidental punctures and injury, both inside and outside the patient's body. Additionally, the interlock or interconnection can be configured to retain the guidewire to the access device so that the guidewire is not misplaced or lost in the patient's body.

The interlock or interconnection can comprise a release member adapted to engage a lock member on either the needle and/or dilator. The lock member releasably locks the needle and dilator hubs together. When the guidewire is advanced by a sufficient extent, the release member cooperates with and releases the lock member to release the dilator hub from the needle hub. Once the lock member is released, the dilator (and possibly the medical article) can be advanced over the needle.

Another aspect of the invention involves an access device for placing a medical article within a body space. The device includes a needle that has a needle body and a dilator coaxially disposed about the needle body. The device further includes a lock member configured to move between a lock state and an unlock state. The lock member connects the needle to the dilator so as to inhibit at least relative axial movement between at least a portion of the needle and at least a portion of the dilator when the lock member is in at least the lock state. The device further includes a guidewire configured to be coaxially disposed within at least a portion of the needle body and a release member configured to engage with the lock member so as to at least move the lock member from the lock state to the unlock state.

Another aspect of the present invention involves a method of locking a guidewire to an access device. The method includes releasably locking a dilator to a needle so as to inhibit at least relative axial movement between at least a portion of the needle and at least a portion of the dilator. The method further includes sliding a release member and guidewire in a distal direction relative to the locked dilator and needle, the guidewire being attached to the release member and engaging the release member with at least one of the dilator and needle so as to unlock the dilator from the needle and inhibit at least relative axial movement between at least a portion of the guidewire and at least a portion of the needle.

Another aspect of the present invention involves an access device for placing a medical article within a body space. The device includes a needle having a needle body, a dilator coaxially disposed about the needle body and having a dilator shaft, a guidewire, and one or more stops disposed between the guidewire and at least one of the needle and the dilator.

In some embodiments, the one or more stops (which can be adjustable) limit the extent to which the guidewire can be moved (e.g., advanced) relative to the needle or inhibit such relative movement (e.g., backwards movement). In some modes, a stop can be disposed at the proximal end of the guidewire to inhibit the proximal end from slipping into the proximal end of the needle (e.g., into the needle hub). In other modes, the stop can be positioned just proximal to the needle hub to help regulate the length of guidewire that can be advanced from the needle tip. In still other modes, the stop can be slid along the guidewire and set in a position thereon (e.g., near the needle hub). Preferably, an interaction (e.g., interference, friction, mechanical coupling, adhesion, etc.) exists between the guidewire and the stop to inhibit relative movement between these components.

Another aspect of the preset invention involves an access device that has a releasable interlock. The interlock inhibits relative rotational movement between a needle and a dilator, at least when the needle is inserted into a patient. By inhibiting such relative rotational movement, side openings in the needle and dilator can be held in alignment to provide a simplified passageway through which the blood or fluid may flow. Thus, when the needle enters a blood vessel or drainage site in the patient, blood or other body fluid quickly flows into a passageway. The resulting blood or fluid flash is visible through the medical article (sheath or catheter) to indicate that the needle tip has entered the vessel or drainage site.

For example, but without limitation, the dilator can comprise, in some embodiments, a dilator hub and dilator having one or more side openings. The dilator hub may have a luer connection and a releasable locking mechanism. The releasable locking mechanism can be configured to releasably engage and secure the dilator to another part, such as the needle hub. When the needle hub and the dilator hub are releasably locked to prevent rotation therebetween, one or more of the side openings in the dilator are aligned with one or more side openings in the needle. The locking mechanism can also be configured to inhibit unintentional relative axial movement between the needle and the dilator.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 3A is a side view of the dilator portion of the embodiment depicted in FIG. 1.

FIG. 3B is a proximal end view of the dilator portion of FIG. 3A.

FIG. 3C is a cross-sectional view of the dilator portion of the embodiment depicted in FIG. 3A, taken along line B-B.

FIG. 4A is a side view of a sheath of the embodiment from FIG. 1.

FIG. 4B is a proximal end view of the sheath of FIG. 4A.

FIG. 5 is a side view of the access device of FIG. 1.

FIG. 9 is an enlarged cross-sectional view of a needle hub with a guidewire extending therethrough, wherein the needle hub and the guidewire are configured in accordance with another preferred embodiment of the present invention.

FIG. 10 is an enlarged cross-sectional view of a needle hub with a guidewire extending therethrough, wherein the needle hub and the guidewire are configured in accordance with a further preferred embodiment of the present invention.

FIG. 14 is an enlarged side view of a proximal end of an access device, including a guidewire with a release mechanism, which are configured in accordance with an additional embodiment of the present invention.

FIG. 15 is an enlarged side view of a proximal end of an access device that is configured in accordance with another embodiment of the present invention.

DETAILED DESCRIPTION OF THE PREFERRED EMBODIMENTS

The present disclosure provides an access device for the delivery of a medical article, for example a catheter or sheath, to a blood vessel or drainage site that overcomes possible disadvantages associated with conventional non-surgical catheter insertion techniques.

Figure 1:
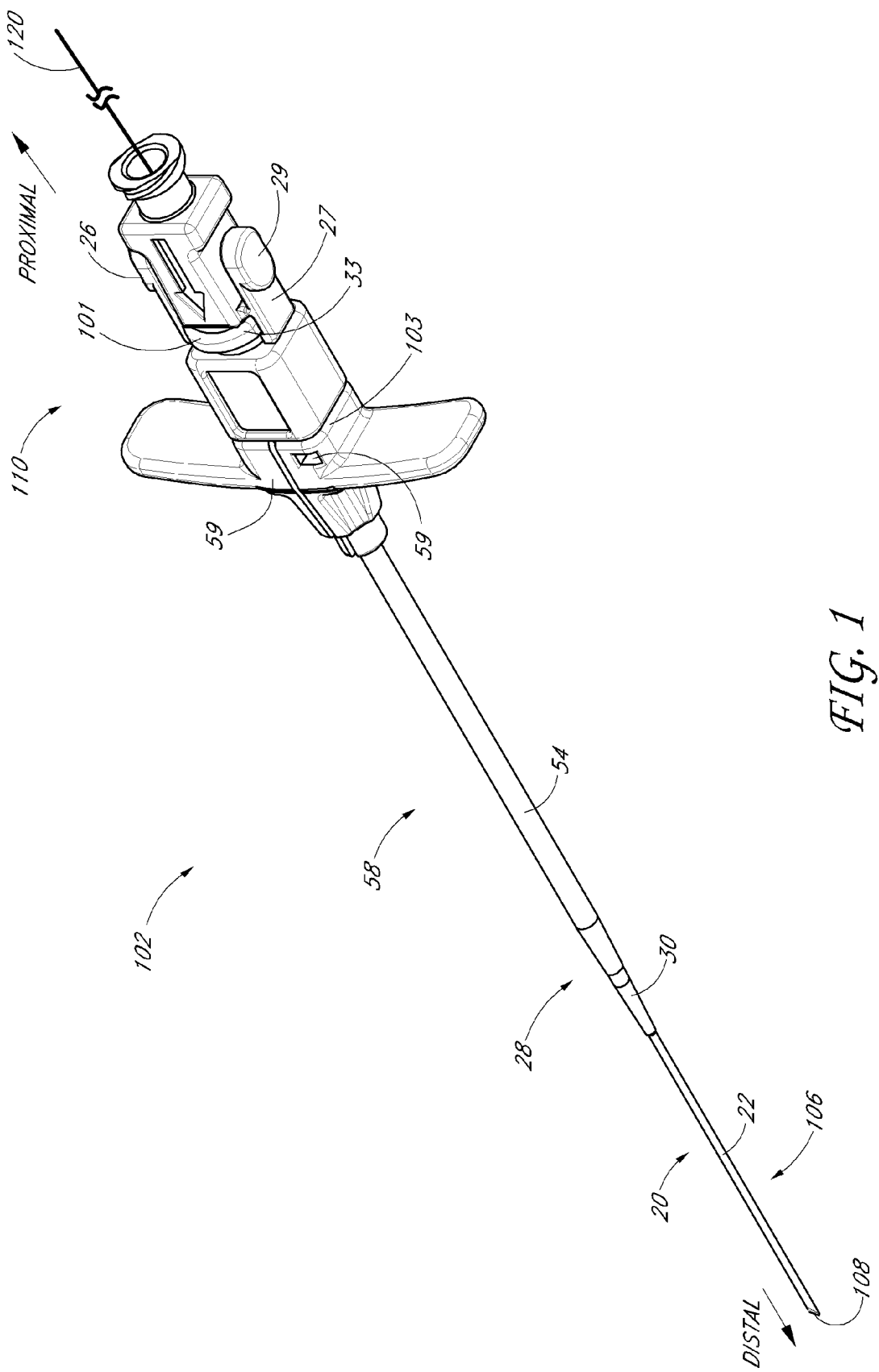
FIG. 1 is a perspective view of a preferred embodiment of an access device configured in accordance with the present invention and shows coaxially aligned needle, dilator, medical article, and guidewire.

The present disclosure provides an access device for the delivery of a medical article (e.g., catheter or sheath) to a blood vessel or drainage site. FIG. 1 illustrates an access device 102 that is configured to be inserted into a blood vessel (e.g., a vein or an artery) in accordance with a preferred embodiment of the present invention. While the access device is described below in this context (i.e., for vascular access), the access device also can be used to access and place a medical article (e.g., catheter or sheath) into other locations within a patient's body (e.g., a drainage site) and for other purposes (e.g., for draining an abscess).

The present embodiment of the access device is disclosed in the context of placing an exemplary single-piece, tubular medical article into a body space within a patient. Once placed, the tubular article can then be used to receive other medical articles (e.g., catheters, guidewires, etc.) to provide access into the body space, and/or used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood by one of skill in this art, in light of the present disclosure, that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can also be configured to directly or indirectly place central venous catheters, peripherally inserted central catheters, hemodialysis catheters, surgical drainage tubes, tear-away sheaths, multi-piece sheaths, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit or passageway into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

The access device 102 comprises a needle 20, a dilator 28, a sheath (e.g., catheter or cannula) 58, and a guidewire 120. In preferred embodiments, the dilator 28 is coaxially mounted on the needle 20, and the sheath 58 is coaxially mounted on the dilator 28.

In the illustrated embodiment, the needle 20, dilator 28, and sheath 58 are releasably interlocked at the proximal end 110 of the access device 102. In some embodiments, the releasable interlock between the needle 20, dilator 28, and sheath 58 is a linear interlock where the dilator 28 is locked to the needle 20 at interface 101 and the sheath 58 is locked to the dilator 28 at interface 103. Preferably, the needle 20 locks to the dilator 28 via a lock mechanism 26. The lock mechanism 26 may comprise an engaging mechanism such as hinged clips 27 with clip sides 29. The hinged clips 27 may releasably engage and secure the dilator 28 to the needle 20. In some embodiments, the clip sides 29 engage and secure the dilator 28 by clipping to the outer lip of a luer connection 33 on the dilator 28. Although hinged clips 27 are shown, the lock member 26 may comprise any suitable engaging mechanism known in the art. In the illustrated embodiment, as best seen in FIG. 3B, the portions of the outer lip onto which the hinge clips 27 engage are flats to inhibit rotation of the needle hub 21 relative to the dilator hub 32 after a certain degree of relative rotation (e.g., 180 degrees) between the needle hub 21 and the dilator hub 32.

Similarly, the sheath 58 is secured to the dilator 28 through a lock member 59. The sheath 58 may, preferably, comprise a twist lock member 59 so that the user may releasably engage and secure the dilator 28 to the sheath 58. In some preferred embodiments, the dilator 28 comprises teeth or prongs that are configured to mate or attach to corresponding areas on the sheath 58. Preferably, the needle 20, dilator 28 and sheath 58 are releasably locked so that a physician or user may remove sections or portions of the access device as needed for treatment.

Figure 2A:
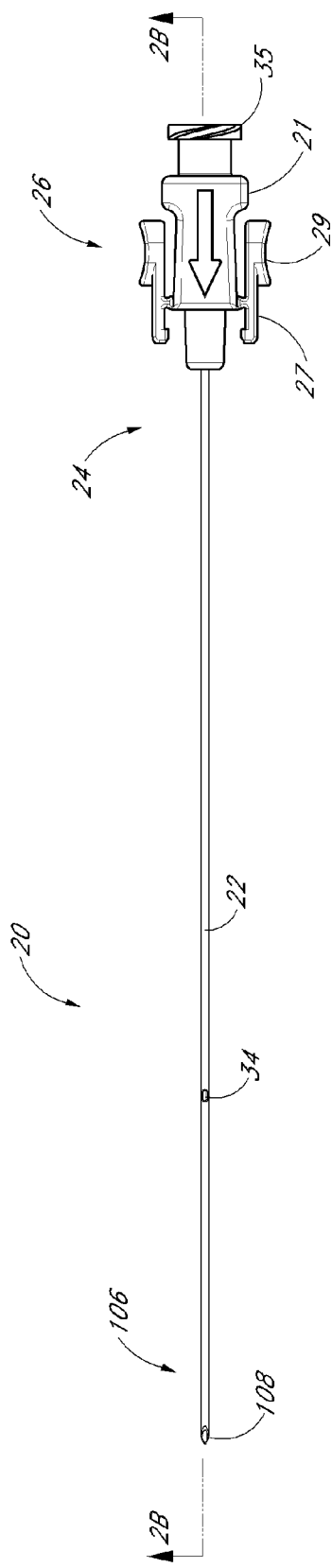
FIG. 2A is side view of a needle of the embodiment depicted in FIG. 1.
Figure 2B:
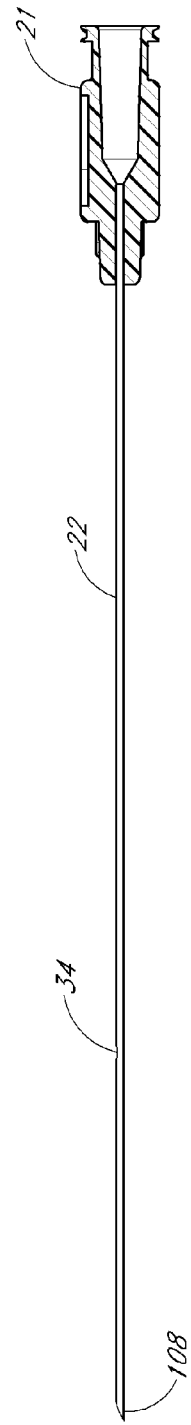
FIG. 2B is a cross-sectional view of the needle of the embodiment depicted in FIG. 2A taken along line A-A.

FIGS. 2A and 2B depict the needle 20 of the preferred embodiment shown in FIG. 1. FIG. 2A shows a side view of the needle 20 and FIG. 2B provides a cross-sectional view of the needle 20. As shown in both FIGS. 2A and 2B, the needle 20 has a needle body 22, distal end 106, and proximal portion 24. Preferably, the proximal portion 24 has a needle hub 21 and the lock member 26.

The needle body 22 preferably has an elongated tubular shape having a circular, constant-diameter inner bore and a circular, constant-diameter exterior surface. In other embodiments, however, the needle body 22 can have other bore and exterior shapes (such as, for example, but without limitation, an oval cross-sectional shape).

The needle body 22 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 22 preferably has a length of 7 cm or greater, and more preferably has a length of 9 cm or greater, and most preferably has a length of 9 to 10 cm. The size of the needle preferably is 18 gauge or smaller, and more preferably between 18-26 gauge, and most preferably between 18-26 gauge. For applications with a neonate, the length and gauge of the needle body 22 should be shorter and smaller, for example preferably between 3-4 cm and between 26-28 gauge.

As best seen in FIGS. 2A and 2B, the needle body 22 includes at least one fenestration or opening 34 near a distal end of the needle body 22. The fenestration 34 extends through the wall of the needle body 22. In addition, the needle body 22 can have a bevel tip 108 disposed on the distal portion 106.

The needle hub 21 may also include locking structures at the proximal portion and distal portion of the needle hub 21. These locking structures may be a luer-thread-type or another type of connections. In the illustrated embodiment, a luer connection 35, such a luer lock or slip, is disposed at the proximal portion 24 of the needle 20. This allows the physician or healthcare provider, for example, to introduce a guidewire 120 through the hollow portion of the luer connection 35, through the needle body 22, and into a punctured vessel. Additionally, a physician or healthcare provider may also attach a syringe to the luer connection 35 to perform other procedures as desired.

As discussed above, in preferred embodiments, the needle hub 21 comprises the lock member 26. The lock member 26 may be configured to lock or secure another part such as, for example, the dilator 28 or the sheath 58, to the needle 20. As shown in FIG. 2A, the lock member 26 can comprise an engaging mechanism such as a pair of hinged clips 27, although other types of locking mechanisms comprising tabs and/or slots can also be used. Preferably, the clip sides 29 of the hinged clips 27 can engage a lipped surface such as the outer lip 37 of a luer connection 33 to the dilator 28, shown in FIG. 1. Once engaged, the clip sides 29 prevent the locked part from undesired slipping or releasing. In certain embodiments, the clips 27 are hinged to provide a bias towards the center of the needle hub 21. Preferably, the bias prevents the secured part from slipping or disengaging from the hinged clips 27. More preferably, the bias of the hinged clips 27 can be overcome by simultaneously applying pressure to or squeezing the sides 29 of the clips 27 to release, for example, a luer connection to the luer connection 33 from the needle hub 21. To apply the appropriate releasing pressure, a physician or healthcare provider may, for example, place an index finger and thumb on the sides 29 of the hinged clips 27 and apply squeezing pressure to overcome the hinge bias. The hinged clips 27 will, preferably, release only when sufficient releasing pressure is applied to both clip sides 29.

The needle proximal portion 24 may have color coding, words, or other indicia, such as a pivot or notch, to indicate to the operator the position of the bevel tip 108 relative to the dilator 28 or the sheath 58. Also, there may be a mechanical fit between the dilator 28 and the needle body 22 so that the physician or healthcare provider would sense by feel or sound (e.g., by a click) when the needle body 22 has been rotated to change the position of the bevel tip 108. The needle body 22 can be rotated relative to the dilator 28 and sheath 58, so that the bevel tip 108 can be inserted into the blood vessel with bevel tip up, and can be rotated 180 degrees so that the bevel tip 108 is down after successful insertion. When the bevel tip 108 is in this position, it may be less likely that movement of the needle body 22 will cause injury to the blood vessel.

FIGS. 3A, 3B, and 3C provide a side view of an entire dilator 28, a side view of the dilator hub 32 from the proximal end 45, and a cross-sectional view of a dilator 28, respectively, for the embodiment described in FIG. 1. As shown, the dilator 28 may comprise a dilator shaft 30 and a dilator hub 32. The dilator shaft 30 may further comprise one or more side openings or fenestrations 111. The dilator hub 32 preferably comprises a luer connection 33 with an outer lip 37. In some embodiments, the outer lip 37 can be configured to engage to a lock member 26 on the needle 20.

Additionally, the dilator shaft 30 may be coaxially mounted to the needle body 22 by slipping the hollow section 113 of the dilator shaft 30 over the needle body 22 and releasably securing the dilator hub 32 to the needle hub 21. Preferably, the proximal end 45 of the dilator hub 32 is configured to mechanically fit and interlock with the needle lock member 26 to inhibit some rotational and axial motion. More preferably, the dilator shaft 30 is releasably mounted to the needle body 22 so that the dilator shaft 30 can be mounted and released, or vice versa, from a coaxial position relative to the needle body 22.

In some embodiments, the dilator hub 32 further comprises a locking mechanism 39. In FIG. 3A, the locking mechanism 39 comprises posts, teeth, or prongs projecting from the dilator hub 32. These teeth 39 can be configured to mate or attach to corresponding receiving areas disposed on another part such as the sheath 58 or the needle hub 21. This locking mechanism 39 will be explained in greater detail in the following section.

FIGS. 4A and 4B show side views of the medical article or sheath 58 illustrated in FIG. 1. FIG. 4B provides a side view from the proximal end 57. The medical article preferably, but not necessarily, includes a sheath 58. In preferred embodiments, the sheath 58 comprises a sheath body 54 and a sheath hub 53. The sheath body 54 may be made partially or completely from a clear, translucent, semi-opaque, or transparent material. Such transparent, translucent, semi-opaque and clear materials allow a clinician the ability to see when blood or other body fluids flows into the needle, through the needle side opening(s), through the side dilator opening(s), and into the viewing space between the dilator and sheath.

The sheath body 54 may be a single piece sheath through which a catheter or other medical article (e.g., a guidewire) is inserted into the vessel. In such an embodiment, the sheath body 54 forms a conduit for insertion of the catheter or other medical article (e.g., a guidewire). In addition to providing a conduit, the sheath or a portion of the sheath can form a lumen that is in addition to the lumen(s) of the catheter. For example, an equivalent to a triple lumen catheter can be formed by inserting a dual lumen catheter through the sheath body 54 with the sheath body 54 itself forming a third lumen. The sheath hub 53 may further comprise winged ends 55 and a lock member 59.

Preferably, the lock member 59 may comprise a locking or attaching structure that mates or engages with a corresponding structure. For example, the lock member 59 may comprise indentations, bumps, or grooves designed to engage and secure the teeth 39 on the dilator hub 32 described above in FIG. 2A. The sheath hub 53, as best seen in FIGS. 4A and 4B, preferably is designed so that the teeth 39 of the dilator hub 32 can enter the sheath hub 53 substantially unobstructed. However, in use, once the sheath hub 53 is placed at a desired location over the dilator shaft 30, the physician or healthcare provider can twist the sheath hub 53 and disengage the locking member 59. The locking member 59 can be, for example, a protruding bump, dent, etc., that creates a mechanical fit so that the dilator hub 32 and the sheath hub 53 are releasably interlocked. In the illustrated embodiment, the locking member 59 of the sheath hub 53 comprises a pair of axial arranged grooves which extend from an end of the sheath hub 53 and terminate at a protruding bump, dent, etc. Preferably, the locked position can be disengaged by twisting the dilator hub 32 relative to the sheath hub 53. Additionally, the sheath hub may comprise wings 55 or handle structures to allow for easy release and removal of the sheath body 54 from other parts.

In some applications, the wings 55 are sized to provide the healthcare provider with leverage for breaking apart the sheath hub 53. For example, the sheath hub 53 may comprise a thin membrane 61 connecting the halves of the sheath hub 53. The membrane 61 is sized to keep the halves of the sheath hub 53 together until the healthcare provider decides to remove the sheath hub 53 from the access device. The healthcare provider manipulates the wings 55 to break the membrane 61 and separate the sheath hub 53 into removable halves.

It may be advantageous to remove a portion or the entire sheath body 54 depending on the type of catheter or medical article that is to be inserted into the vessel after employing the access device 102. For example, after the catheter or other medical article is inserted into the vessel, a portion of the sheath body 54 can be separated or peeled-away and removed. A peel-away sheath can include perforations, serrations, or other material structure to allow the physician or healthcare provider to easily remove a portion or the entire sheath body 54.

FIG. 5 depicts a side view of the assembled access device 102 in which the needle 20, dilator 28, and sheath 58 are interlocked together. In the assembly, as noted above the needle 20, dilator 28 and sheath 58 are coaxially disposed about a common longitudinal axis.

Figure 6:
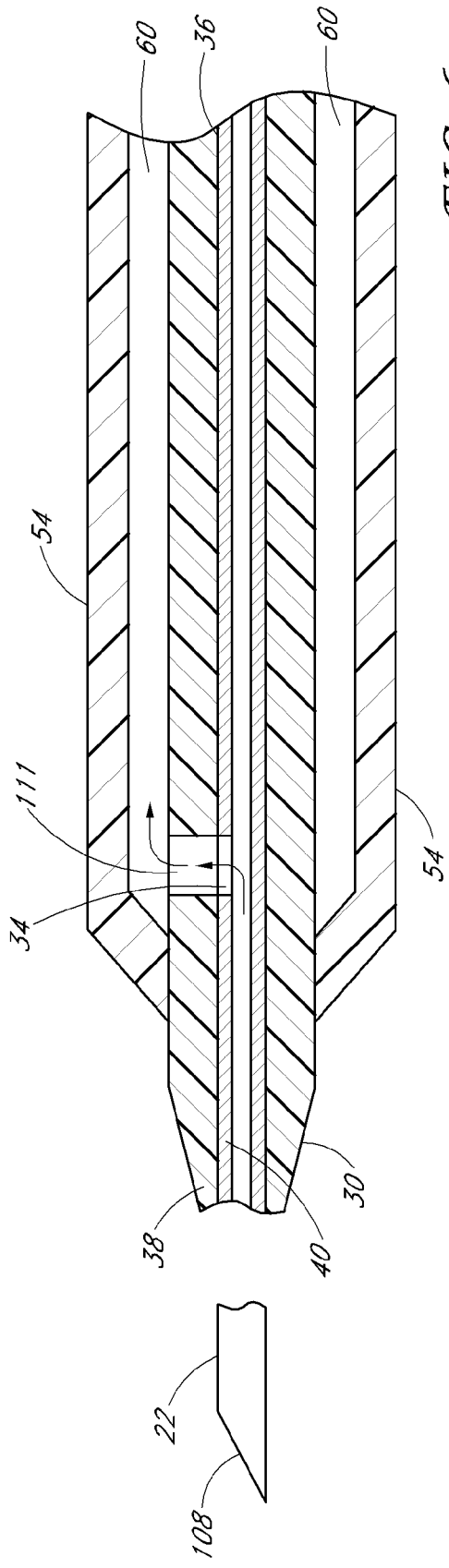
FIG. 6 is an enlarged cross-sectional view of a portion the embodiment illustrated in FIG. 5 which is circled by line C-C.

FIG. 6 depicts a partial cross-sectional view of the assembled unit. As noted above, the needle body 22, preferably, comprises one or more side openings 34 in its side wall. Additionally, the dilator may comprise one or more side openings 111. FIG. 6, however, illustrates the alignment between only one set of corresponding side openings. Other sets of side openings can also be aligned or be misaligned depending upon the relative orientations of the needle 20 and the dilator 28.

Preferably the dilator shaft 30 may be coaxially positioned to minimize the annular space 36 between the needle body 22 and the dilator shaft 30. The inner surface 38 of the dilator shaft 30 need not, though it can, lie directly against the outer-surface 40 of the needle body 22. Preferably, the annular interface 36 between the outer-surface 40 of the needle body 22 and the inner surface 38 of the dilator shaft 30 is minimized to inhibit the flow of blood or its constituents (or other bodily fluids) into the annular interface 36 between the dilator shaft 30 and needle body 22. Advantageously, this feature minimizes the blood's exposure to multiple external surfaces and reduces the risk of contamination, infection, and clotting.

The sheath body 54 is made partially or completely from clear, semi-opaque, translucent, or transparent material so that when blood flows into the needle body 22, (1) through the needle side opening 34, (2) through the dilator side opening 111, and (3) into an annular space 60 between the dilator shaft 30 and the sheath body 54, the physician or healthcare provider can see the blood. This will indicate to the physician or healthcare provider that the bevel tip 108 of the needle body 22 has punctured a blood vessel.

More preferably, the dilator shaft 30 can be coaxially mounted to the needle body 22 such that at least one side opening 34 disposed on the needle body 22 is rotationally aligned with at least one side opening 111 on the dilator shaft 30. In some embodiments, the needle body 22 and dilator shaft 30 may (both) have multiple side openings 34, 111 where some or all of these side openings 34, 111 can be rotationally aligned. Preferably, the needle body 22 and dilator shaft 30 maintain rotational alignment so that blood flows substantially unobstructed through the needle side opening 34 and dilator side opening 111.

In some embodiments, the dilator shaft 30 and needle body 22 maintain releasable rotational alignment where the user may transition the dilator shaft 30 and needle body 22 from a first annular position to a second annular position about the longitudinal axis relative to the needle body 22. The transition from a first to second position may align or misalign the respective side openings on the needle body 22 and dilator shaft 30. This feature allows the user to change the needle body 22 to a desired orientation before and/or after puncturing the blood vessel. For example, as discussed above, generally, it is preferred that the bevel tip 108 enter the vessel with bevel tip 108 up. However, once the needle body 22 is in the vessel, rotating the bevel tip 108 180 degrees prevents risk of unwanted injury to the vessel. In preferred embodiments, the physician or healthcare provider can alter the rotational alignment between the dilator shaft 30 and needle body 22 according to his/her needs.

Figure 7:
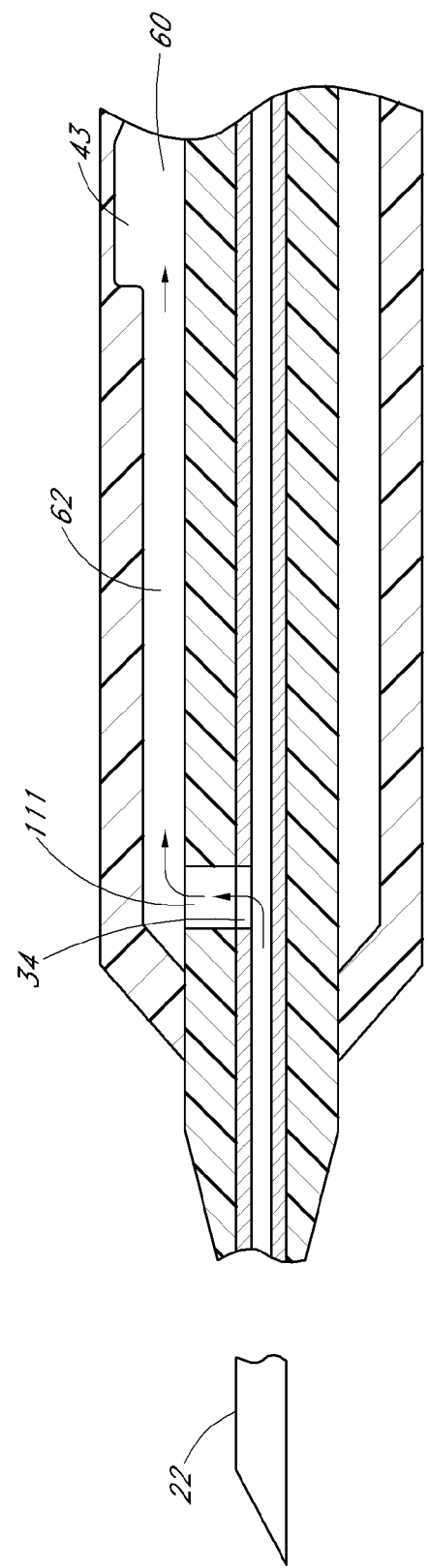
FIG. 7 is a similar cross-sectional view of a portion of an access device which is configured in accordance with another preferred embodiment of present invention.

FIG. 7 depicts a cross-sectional view of another preferred embodiment of the present invention. Additionally or alternatively, the annular space 60 between the dilator shaft 30 and sheath body 54 may be minimized to reduce the flow of blood into this space 60. Preferably, a passageway or conduit 62 is provided that channels blood flow to a view space 43. A groove formed (e.g., by scoring) on either the outer side of the dilator shaft 30 or the inner side of the sheath body 54 can define at least a portion of the passageway or conduit 62. In the illustrated embodiment, the passageway or conduit 62 and the view space 43 reduce the open space in the annular space 60 into which the blood or fluid can flow.

Figure 8:
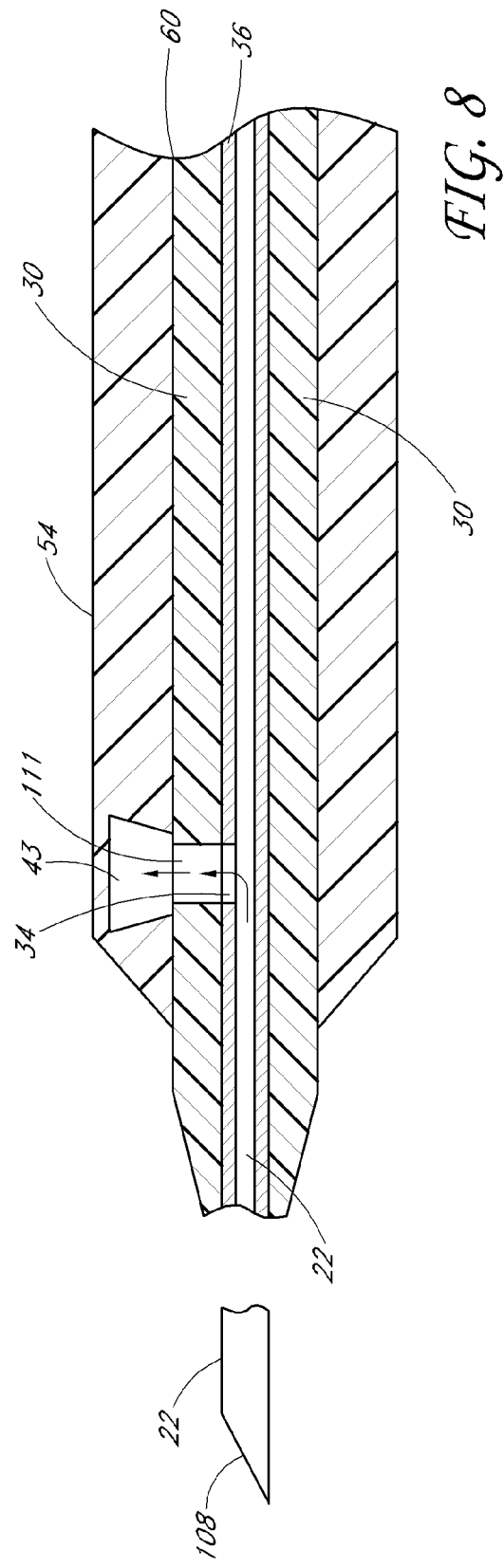
FIG. 8 is a similar cross-sectional view of a portion of an access device which is configured in accordance with an additional preferred embodiment of present invention.

FIG. 8 depicts a cross-sectional view of another preferred embodiment of the present invention. In some embodiments, the annular space 60 can be substantially restricted so that blood or its constituents cannot flow into the annular space between the sheath body 54 and the dilator shaft 30. The sheath, preferably, comprises a view space 43 that allows some blood to flow into a substantially reduced space between the dilator shaft 30 and sheath body 54. Preferably, blood cannot flow from the view space 43 or side openings 34, 111 into the annular space 60. The portion of the sheath body 54 above the view space 43 can be made from a clear, semi-opaque, translucent, or transparent material so that when blood flows into the needle body 22, through the needle side opening 34, through the dilator side opening 111, and into the view space 43, the physician or healthcare provider can see the blood. Most preferably, the dilator side opening 111, needle side opening 34, and the view space 43 are rotationally aligned so that the blood can flow through the needle side opening 34, through the dilator side opening 111, and into the view space 43 without any substantial obstruction. In some embodiments, the sheath may comprise more than one view space 43.

While the side openings 34, 111 in the needle 20 and the dilator shaft 30 are aligned in the embodiments illustrated in FIGS. 6, 7 and 8, the side openings alternatively can overlap with each other or can be connected via a passageway or conduit 62. The passageway or conduit 62 can be formed between the side openings 111, 34 in the dilator and the needle. In some embodiments of the access device, the passageway or conduit 62 is defined by one or more grooves that are formed (e.g., by scoring) on an outer side surface of the needle, on an inner side surface of the dilator, or on both the needle outer side surface and the dilator inner side surface. In this latter form, the grooves can oppose each other or can overlap at one or more points to define a portion of the passageway. In additional embodiments, the passageway or conduit 62 that places the side openings in communication can be formed by incongruous shapes (e.g., incongruous radial cross-sectional shapes) between the needle outer surface and the dilator inner surface. For example, the needle outer surface can have a circular shape and the dilator inner surface can have an oval shape with a minor dimension of the oval substantially equals the diameter to the circle, or vise versa. The needle outer surface and the dilator inner surface also can have other incongruous shapes, such as, but without limitation, a triangle and a circle, a square and a circle, and a square and a triangle, where the needle supports the dilator at least at two points.

In accordance with another aspect of the present invention, there is provided an interlock or interconnection between the guidewire and at least one of the following components of the access device: (1) the needle body; (2) the needle hub; and (3) the dilator hub. The interlock or interconnection inhibits the proximal end of the guidewire from being advanced too far into the needle (and risk the possibility of intravascular guidewire loss), as well as allows the needle, the dilator and the guidewire to be generally withdrawn simultaneously. Additionally, by inhibiting the withdrawal of the advanced guidewire back into the needle, the risk of shearing off the distal end of the guidewire and having a guidewire embolus is reduced. The interlock or interconnection can also ensure that the distal end of the guidewire remains extended beyond the distal end of the needle to protect the needle tip, thereby inhibiting an accidental needle stick.

FIG. 9 illustrates an embodiment of an interconnection suitable to couple the guidewire 120 with the needle hub 21 once a healthcare provider has advanced the guidewire 120 to its fully deployed position (i.e., to a position where the guidewire 120 extends well beyond the distal end 108 of the needle body 22 into the vessel). In the illustrated embodiment, the interconnection comprises a female luer or inner bore 130 defined by the inner bore of the needle hub 21 and a male luer 122 disposed on the guidewire 120. The male luer 122 preferably resided at the proximal end of the guidewire 120; however, it can be formed at other locations along the guidewire's length, provided a sufficient length of guidewire 120 extends into the vascular lumen (or other body cavity, lumen or space) when the male luer 122 engages the female luer 130.

The male luer 122 can be molded (e.g., inserted molded), crimped, adhered or otherwise attached onto or to the end of the guidewire 120 or can be formed in a unitary manner with the guidewire 120. For example, the male luer body 122 can be molded as a separate piece with a hole passing through the luer body 122. The hole can be created in the molding process or can be created thereafter. The luer body 122 is then threaded over the guidewire 120. The proximal end of the guidewire can be crimped, kinked, or enlarged by the addition of other material to inhibit the luer body 122 from slipping off the proximal end of the guidewire 120. The guidewire 120 can be similarly modified at a point distal of the luer body 122 to inhibit the luer body 122 from sliding distally and ease the use of the device; however, such further modification is unnecessary in order to interconnect together the needle hub 21 and guidewire 120 when the guidewire 120 is fully deployed.

The male and female luer connection illustrated in FIG. 9 is but one example of the types of cooperating structure that can be included to interconnect or interlock the guidewire 120 with the needle hub 21. Other types of interengaging structure can also be used for this purpose. For example, but without limitation, the guidewire 120 can include one or more enlarged beads at or near its proximal end and the needle hub 21 can include one or more annular grooves defined about its conical inner bore 130. When advancing the guidewire 120 to its fully extended position, the bead snaps into the corresponding annular groove to interlock the guidewire 120 to the needle hub 21.

The engagement between the guidewire 120 and the needle hub 21 can occur through simple axial movement of the guidewire 120 relative to the needle hub 21, as understood from the embodiments described above. It can also occur through relative rotational movement between the guidewire 120 and the needle hub 21, or though a combination of both axial and rotational movements. For example, the male luer 122, which is included on the end of the guidewire 120, can include one or more projecting structures (e.g., an external thread) that engage one or more spiral grooves (e.g., an internal thread) formed within the needle hub 21. A combined axial and rotational movement of the guidewire 120 relative to the needle hub 21 will interengage these cooperating structures to interlock the guidewire 120 and the needle hub 21.

FIG. 10 illustrates another interlock formed between the guidewire 120 and the needle hub 21. In this embodiment, the proximal end of the guidewire 120 is shaped as a clip 140, which is configured to engage structure on the needle hub 21. In the illustrated embodiment, the clip 140 has a two-dimensional shape; however, in other embodiments, the clip can take a three-dimensional shape.

As shown in FIG. 10, the clip 140 is preferably configured to engage an annular flange 142 disposed at the end of the needle hub 21. For this purpose, the clip 140 includes a transverse section 144 that extends outwardly from a longitudinal axis of the guidewire 120 and lies generally normal to the longitudinal axis; however, the transverse section 144 can extend at an acute or oblique angle relative to the longitudinal axis of the guidewire 120. The length of the transverse section preferably is slightly larger than half of the diameter across the hub flange 142.

The clip 140 also includes a spring clip 146 that extends distally from the transverse section 144. The spring clip 146 includes a generally V-shaped end that is configured to deflect outwardly and ride over the hub flange 142 when the guidewire 120 is advanced distally and then to spring back toward the guidewire 120 and into a groove or space provided on a distal side of the hub flange 142. While not illustrated, the spring clip 146 can include an abutment surface on an inner side of the spring clip 146, which extends generally normal to the longitudinal axis and is disposed to abut against a distal side of the hub flange 142 to resist proximal movement of the guidewire 120 relative to the needle hub 21.

Figure 11:
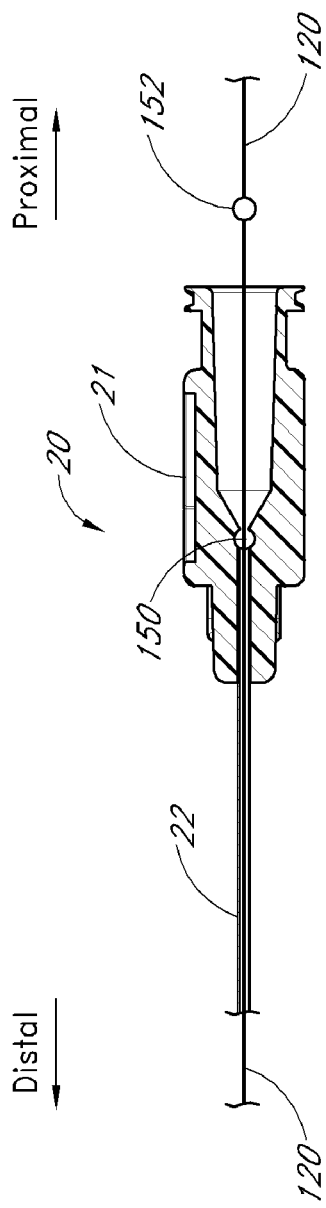
FIG. 11 is an enlarged cross-sectional view of a needle hub with a guidewire extending therethrough, wherein the needle hub and the guidewire are configured in accordance with an additional preferred embodiment of the present invention.

FIG. 11 illustrates an example of an interlock formed between the guidewire 120 and the needle body 22. The interlock is formed in part by a hole 150 through the needle body 22. In the illustrated embodiment, hub material on either side of the through hole 150 is also omitted; however, such a relief may not be included in other embodiments. Additionally, the hole 150 need not extend through the needle body 22.

Figure 12:
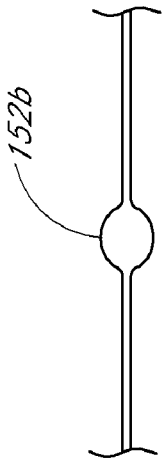
FIG. 12 is an enlarged view of a section of a guidewire configured in accordance with a further preferred embodiment of the present invention.
Figure 13:
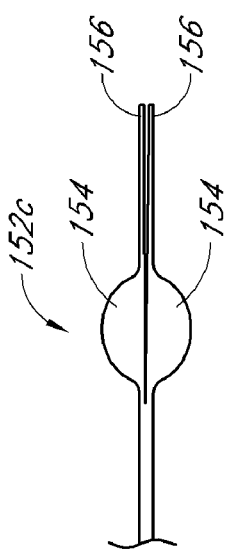
FIG. 13 is an enlarged view of a section of a guidewire configured in accordance with another preferred embodiment of the present invention.

The guidewire 120 includes a protuberance 152 (e.g., a bead) formed along its length which is deformable and is slightly larger than the inner diameter of the needle body 22. The protuberance 152 may be integral with the guidewire 120 or be attached to the guidewire 120. The protuberance 152 can also take the form of a deflectable barb that projects proximally from the guidewire 120 to inhibit proximal movement once it engages with the through hole 150. Additional protuberances are depicted in FIGS. 12 and 13. In FIG. 12, the protuberance 152b is formed by flattening a section of the guidewire 120. In FIG. 13, the protuberance 152c is formed by a pair of nubs 154 formed on opposite sides of the guidewire 120. The guidewire is split to a point distal of the nubs and plastically deformed so as to spread the nubs 154 apart. The split ends 156 of the guidewire 120 act as leaf springs that bias the nubs 154 outwardly, away from a longitudinal axis of the guidewire 120.

With reference back to FIG. 11, the protuberance 152 is sized and located on the guidewire 120 to interact with the through hole 150 once the guidewire 120 has been advanced into the vessel by a desired length. At this point, the protuberance 152 snaps or springs into one or both sides of the through hole 150 to hold the guidewire 120 relative to the needle body 22. The guidewire 120 can also include a plurality of protuberances so as to provide multiple extension lengths for the guidewire 120 from the needle body 22 and/or to interact with a plurality of through holes to provide enhanced or redundant interengagement between the guidewire 120 and the needle body 22.

FIG. 14 illustrates a further embodiment of an interlock between the guidewire 120 and the needle hub 21 with the addition of a release mechanism that unlocks the dilator shaft 30 (and the sheath body 54 in the illustrated embodiment) from the needle hub 21. The proximal end of the guidewire 120 is attached to an end cap 160 that interacts with the needle hub 21 in any of the variety of ways described above. The end cap 160 additionally includes a pair of cam arms 162. The cam arms 162, when the end cap 160 is engaged with the needle hub 21, cause the clip sides 29 to depress inward and release the hinged clips 27 from the flange 33 of the dilator hub 32. In this position, the guidewire 120 is interlocked or interconnected with the needle hub 21, while the dilator shaft 30 is free to be advanced over the needle body 22.

FIG. 15 illustrates a further embodiment of an access device that includes an interconnection between the guidewire 120 and the needle hub 21, which also helps support a length of guidewire 120 before insertion into the needle body 22. In this embodiment, a support rod 170 extends proximally from the needle hub 21. In some embodiments, the length of the rod 170 can generally equal the length of the guidewire 120 and in other embodiments it can be significantly shorter (e.g., 25%-50% of the guidewire's length). The guidewire 120 includes a loop 172 formed at or near its proximal end which slides over the rod 170 as the guidewire 120 is advanced into the needle body 22. The interaction between the loop 172 and the rod support 170 supports the proximal end of the guidewire 120. This same interaction inhibits withdrawal of the guidewire 120 from the needle 20 once the guidewire 120 is fully advanced. In another embodiment, the loop can be part of the rod and the guidewire is placed within that loop, reducing the likelihood that the wire will fall out of the device before or during the procedure.

Figure 16:
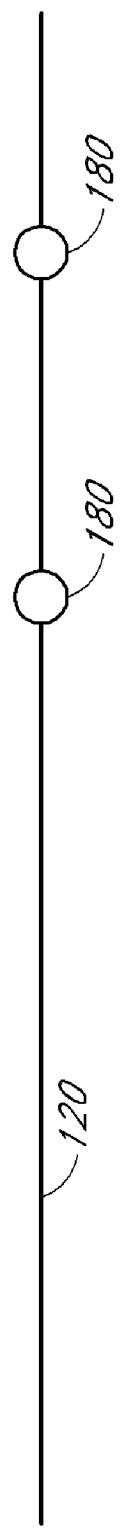
FIG. 16 is a side view of a guidewire configured in accordance with another embodiment of the present invention.

FIG. 16 illustrates another embodiment of a guidewire 120 that can be used with one or more of the above-described embodiments of the access device. The guidewire 120 has one or more movable positioners or stops 180 that can be slid along the guidewire shaft 120 as desired to limit the forward advancement or backward movement of the guidewire 120 within the assembly of the needle 20, the dilator 28, and the sheath 58. In the illustrated embodiment, the stops 180 are silicone balls. The stop(s) of course can have other shapes as well such as, for example, but without limitation, a hollow cylindrical shape or a hollow truncated conical shape (e.g., substantially matching the shape of the needle hub inner bore), and can be made of other types of materials as well.

Each ball 180 in the illustrated embodiment has a bore 182 passing through the ball 180. The bore 182 has a diameter approximately equal to the diameter of the guidewire 120. The compressible nature of the silicone balls 180 allows them to be slid under force to a desired location along the guidewire's length. Once a sufficient sliding force is no longer applied, the interference and resulting friction between the balls 180 and the guidewire 120 inhibits the balls 180 from sliding over the guidewire 120. Additionally, one or more of the stops 180 can be split along its length (e.g., by a groove, slit, or elongated opening) that permits the stop to be attached and detached from the guidewire 120 without passing over an end of the guidewire 120. This configuration thus allows the stop(s) 180 to be removed from guidewires with outwardly-extending proximal structure (e.g., the guidewires 120 shown in FIGS. 9, 10, 14 and 15) without passing over either the proximal or distal ends of the guidewire.

The outer diameter of the balls 180 is sized to be larger than the proximal opening into the needle body 22. In the illustrated embodiment, the outer size of the ball 180 is larger than an inner bore 130 of the needle hub 21; however, in other embodiments, the ball 180 can be sized to fit within the inner bore 130 but not to fit into the needle body 22. The resulting interference between the stop 180 and the needle hub 21 and/or the needle body 22 limits the forward advancement of the guidewire 120 into the needle 20, as well as inhibits retraction (backwards movement) of the guidewire 120 from the needle body 22. The balls 180 also support the guidewire 120 when the access device 102 is placed in its packaging, and inhibit the guidewire 120 from moving relative to the needle/dilator/sheath assembly during sterilization, transport and storage, prior to use.

The embodiments herein described are comprised of conventional, biocompatible materials. For example, the needle preferably consists of a rigid polymer or a metal such as stainless steel, nitinol, or the like. The other elements can be formed of suitable polymeric materials, such as polycarbonate, nylon, polyethylene, high-density polyethylene, polypropylene, fluoropolyrners and copolymers such as perfluoro (ethylene-propylene) copolymer, polyurethane polymers or co-polymers.

As noted above, the present access device can be used to place a catheter at other locations within a patient's body. Thus, for example, but without limitation, the access device can be used as or with a variety of catheters to drain fluids from abscesses, to drain air from a pneurnotorax, and to access the peritoneal cavity. In such applications, body fluids flow into the viewing space to indicate when the needle has been properly placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

What is claimed is:

1. An access device for placing a medical article within a body space, comprising:
    a needle having a needle body and an interior bore;
    a dilator coaxially disposed about the needle body and having a dilator shaft;
    a medical article coaxially disposed about the dilator;
    a plurality of openings extending through a side of at least one of the needle body and the dilator shaft;
    at least one opening in the other one of the needle body and dilator shaft, the plurality of openings being spaced about the one of the needle body or dilator shaft so that at least one of the plurality of openings at least partially overlaps the at least one opening in the other one of the needle body and dilator shaft when the needle body is rotationally clocked relative to the dilator shaft in a first position and in a second position, the second position being different than the first position;
    a viewing space disposed between the dilator and the medical article;
    at least one passageway connecting the viewing space with the interior bore of the needle body, the passageway being defined at least in part by the plurality of openings and the at least one opening;
    a lock member configured to move between a lock state and an unlock state, the lock member connecting the needle to the dilator so as to inhibit at least relative axial movement between at least a portion of the needle and at least a portion of the dilator when the lock member is in at least the lock state; and
    a guidewire configured to be coaxially disposed within at least a portion of the needle body, the guidewire comprising a release member separable from the lock member and configured to engage with the lock member so as to at least move the lock member from the lock state to the unlock state when the guidewire is coaxially advanced within the needle body.

2. The access device of claim 1, wherein the medical article is a catheter.

3. The access device of claim 1, wherein the medical article is a sheath.

4. The access device of claim 3, wherein the sheath comprises a body and a hub.

5. The access device of claim 3, wherein at least a portion of the sheath is clear.

6. The access device of claim 3, wherein at least a portion of the sheath is translucent.

7. The access device of claim 3, wherein at least a portion of the sheath is semi-opaque.

8. The access device of claim 3, wherein at least a portion of the sheath is transparent so as to provide a visual indication when blood or other body fluids flow into the needle body, through the plurality of openings and the at least one opening, and into the viewing space.

9. The access device of claim 1, wherein at least one of the plurality of openings at least partially overlaps the at least one opening in the other one of the needle body and dilator shaft regardless of a rotational orientation of the dilator shaft relative to the needle body.

10. The access device of claim 1, wherein the plurality of openings is irregularly spaced about the one of the needle body or dilator shaft.

11. The access device of claim 1, wherein the at least one opening and the plurality of openings define a plurality of passageways, each passageway connecting the viewing space with an interior bore of the needle body.

12. The access device of claim 1, wherein the at least one passageway has an incongruous shape between the needle outer surface and the dilator inner surface, the incongruous shape being a radial cross-sectional shape.

13. The access device of claim 12, wherein an inner side surface of the dilator shaft has an oval shape and an outer side surface of the needle body has a circular shape.

14. The access device of claim 1, wherein the viewing space is disposed at a distal portion of the medical article.

15. The access device of claim 1, wherein at least a portion of the viewing space has a linear shape along at least a portion of an axial length of the medical article.

16. The access device of claim 1, wherein at least a portion of the viewing space has a curved shape along at least a portion of an axial length of the medical article.

17. The access device of claim 1, wherein at least a portion of the viewing space has a spiral shape along at least a portion of an axial length of the medical article.

18. The access device of claim 1, wherein the viewing space has an annular shape.

19. The access device of claim 18, wherein an axial length of the viewing space is substantially coextensive with a length of the medical article.

20. The access device of claim 18, wherein an axial length of the viewing space is substantially less than a length of the medical article.

21. An access device for placing a medical article within a body space, comprising:
    a needle having a needle body;
    a dilator coaxially disposed about the needle body and having a dilator shaft;
    a lock member configured to move between a lock state and an unlock state, the lock member connecting the needle to the dilator so as to inhibit at least relative axial movement between at least a portion of the needle and at least a portion of the dilator when the lock member is in at least the lock state;

a guidewire configured to be coaxially disposed within at least a portion of the needle body, the guidewire comprising a release member separable from the lock member and configured to engage with the lock member so as to at least move the lock member from the lock state to the unlock state when the guidewire is coaxially advanced within the needle body; and an interlock between the guidewire and at least one of the needle and the dilator.

22. The access device of claim 21, wherein the interlock is configured to retain the guidewire to the access device.

23. The access device of claim 21 further comprising a medical article coaxially disposed about the dilator.

24. The access device of claim 21, wherein the interlock comprises an attachment connecting the guidewire to at least one area of at least one of the needle and the dilator.

25. The access device of claim 24, wherein the one area is a surface on the needle body.

26. The access device of claim 24, wherein the needle includes a needle hub, the one area being a surface on the needle hub.

27. The access device of claim 24, wherein the dilator includes a dilator hub, the one area being a surface on the dilator hub.

28. The access device of claim 24, wherein the attachment connects the guidewire to at least two areas, the two areas being on one of the needle, the dilator, and the needle and the dilator.

29. The access device of claim 24, wherein the attachment is disposed relative to the guidewire so that the guidewire does not have a full range of motion in at least one direction when moving axially relative to the needle body.

30. The access device of claim 24, wherein the attachment is disposed relative to the guidewire so that the guidewire is limited in moving in a proximal direction so as to prevent the guidewire from completely retracting into the needle body.

31. The access device of claim 24, wherein the attachment is disposed relative to the guidewire so that the guidewire is limited in moving in a distal direction so as to prevent the guidewire from completely exiting the needle body.

32. The access device of claim 24, wherein the attachment is disposed relative to the guidewire so that the guidewire is limited in moving in a distal direction so as to maintain a minimum length of the guidewire beyond a tip of the needle.

33. An access device for placing a medical article within a body space, comprising:

a needle having a needle body;

a dilator coaxially disposed about the needle body;

a lock member configured to move between a lock state and an unlock state, the lock member connecting the needle to the dilator so as to inhibit at least relative axial movement between at least a portion of the needle and at least a portion of the dilator when the lock member is in at least the lock state; and a guidewire configured to be coaxially disposed within at least a portion of the needle body, the guidewire comprising a release member separable from the lock member and configured to engage with the lock member so as to at least move the lock member from the lock state to the unlock state when the guidewire is coaxially advanced within the needle body.

34. The access device of claim 33, wherein the release member is configured so that as the release member is moved from a separated position to engage with the lock member to move the lock member to the unlock state, the guidewire simultaneously moves with the release member.

35. The access device of claim 33, wherein the release member is configured so that when the release member engages with the lock member and moves the lock member to the unlock state, at least relative axial movement between at least a portion of the guidewire and at least a portion of at least one of the needle and the dilator is inhibited.

36. The access device of claim 33, wherein the lock member is attached to the needle and releasably attaches to the dilator.

37. The access device of claim 33, wherein the lock member is attached to the dilator and releasably attaches to the needle.

38. The access device of claim 33, wherein each of the needle and the dilator comprises a hub, the lock member connecting the hubs.

39. The access device of claim 33, wherein the guidewire comprises an end cap, the end cap comprising the release member.

40. An access device for placing a medical article within a body space, comprising:

a needle having a needle body;

a dilator coaxially disposed about the needle body and having a dilator shaft;

a lock member configured to move between a lock state and an unlock state, the lock member connecting the needle to the dilator so as to inhibit at least relative axial movement between at least a portion of the needle and at least a portion of the dilator when the lock member is in at least the lock state;

a guidewire configured to be coaxially disposed within at least a portion of the needle body, the guidewire comprising a release member separable from the lock member and configured to engage with the lock member so as to at least move the lock member from the lock state to the unlock state when the guidewire is coaxially advanced within the needle body; and one or more stops disposed between the guidewire and at least one of the needle and the dilator.

41. The access device of claim 40, wherein the one or more stops have a maximum circumference that is greater than a minimum circumference of the guidewire.

42. The access device of claim 40, wherein the one or more stops comprise silicon.

43. The access device of claim 40, wherein the one or more stops have a generally round shape.

44. The access device of claim 40, wherein the one or more stops contacts an inner surface on the needle body at least when the guidewire is slid in a distal direction.

45. The access device of claim 40, wherein the one or more stops is disposed so as to connect the guidewire to at least an area of one of the needle and the dilator.

46. The access device of claim 40, wherein the one or more stops is disposed on the guidewire so that the guidewire does not have a full range of motion in at least one direction when moving axially relative to the needle body.

47. The access device of claim 40, wherein the one or more stops is disposed on the guidewire so that the guidewire is limited in moving in a proximal direction to prevent the guidewire from completely retracting into the needle body.

48. The access device of claim 40, wherein the one or more stops is disposed on the guidewire so that the guidewire is limited in moving in a distal direction to prevent the guidewire from completely exiting the needle body.

49. The access device of claim 40, wherein the one or more stops is disposed on the guidewire so that the guidewire is limited in moving in a distal direction to maintain a minimum length of the guidewire beyond a tip of the needle.

50. The access device of claim 40 further comprising a medical article coaxially disposed about the dilator.

51. The access device of claim 40, wherein the one or more stops are attached to the guidewire.

52. The access device of claim 51, wherein the one or more stops are movable along a length of the guidewire.

53. The access device of claim 51, wherein the one or more stops are inhibited from moving along the length of the guidewire.

54. The access device of claim 51, wherein an interference fit exists between the one or more stops and the guidewire.

55. The access device of claim 51, wherein a friction fit exists between the one or more stops and the guidewire.

56. The access device of claim 51, wherein the one or more stops are mechanically coupled to the guidewire.

57. The access device of claim 51, wherein the one or more stops are adhered to the guidewire.

58. An access device for placing a medical article within a body space, comprising:

a needle having a needle body;

a dilator coaxially disposed about the needle body;

a lock member configured to move between a lock state and an unlock state, the lock member connecting the needle to the dilator so as to inhibit at least relative axial movement between at least a portion of the needle and at least a portion of the dilator when the lock member is in at least the lock state; and a guidewire configured to be coaxially disposed within at least a portion of the needle body, the guidewire comprising a release member separable from the lock member and configured to engage with the lock member so as to at least move the lock member from the lock state to the unlock state when the guidewire is coaxially advanced within the needle body wherein the lock member comprises hinged clips that releasably attach to at least one of the needle and dilator, and the release member is configured to engage the hinged clips to rotate the clips and cause them to release the at least one of the needle and the dilator.

\* \* \* \* \*